(12) United States Patent
Fojtik

(10) Patent No.: US 8,992,482 B2
(45) Date of Patent: Mar. 31, 2015

(54) SYRINGE WITH FLOW CONTROL VALVES AND ASSOCIATED METHODS

(75) Inventor: Shawn P. Fojtik, Park City, UT (US)

(73) Assignee: Control Medical Technology, LLC, Park City, UT (US)

( * ) Notice: Subject to any disclaimer, the term of this patent is extended or adjusted under 35 U.S.C. 154(b) by 375 days.

(21) Appl. No.: 12/723,610

(22) Filed: Mar. 12, 2010

(65) Prior Publication Data

US 2011/0224642 A1    Sep. 15, 2011

(51) Int. Cl.
| | |
|---|---|
| A61M 5/00 | (2006.01) |
| A61M 5/20 | (2006.01) |
| A61B 10/02 | (2006.01) |
| A61M 1/00 | (2006.01) |
| A61M 5/315 | (2006.01) |
| A61M 5/31 | (2006.01) |

(52) U.S. Cl.
CPC ............ *A61M 5/204* (2013.01); *A61B 10/0283* (2013.01); *A61M 1/0009* (2013.01); *A61M 5/31511* (2013.01); *A61M 2005/3112* (2013.01); *A61M 2005/3114* (2013.01); *A61M 2005/3115* (2013.01); *A61M 2005/3128* (2013.01); *A61B 2010/0258* (2013.01)
USPC ........................................................ 604/187

(58) Field of Classification Search
CPC ................... A61M 2005/3128; A61M 5/3148; A61B 5/153; A61B 10/0045
USPC ........... 604/187, 236, 218, 183; 600/578, 579
See application file for complete search history.

(56) References Cited

U.S. PATENT DOCUMENTS

| | | | |
|---|---|---|---|
| 514,900 A | | 2/1894 | Black |
| 657,440 A | * | 9/1900 | McCaw ......................... 604/183 |
| 1,263,299 A | | 4/1918 | Wemhoener |
| 1,882,235 A | | 10/1932 | Spriggs |

(Continued)

FOREIGN PATENT DOCUMENTS

| | | |
|---|---|---|
| CN | 1826149 A | 8/2006 |
| GB | 351272 | 6/1931 |

(Continued)

OTHER PUBLICATIONS

International Searching Authority, U.S. Patent and Trademark Office "International Search Report and Written Opinion" mailed May 5, 2011, in related PCT application No. PCT/US2011/028098.

(Continued)

*Primary Examiner* — Aarti B Berdichevsky
*Assistant Examiner* — Bradley Osinski
(74) *Attorney, Agent, or Firm* — Durham Jones & Pinegar Intellectual Property Law Group

(57) ABSTRACT

The present invention includes syringes with valves. The valves control communication between the interior of a barrel of the syringe and the exterior of the barrel. In syringes that include two valves, the valves may be oriented opposite one another, such that one of the valves may enable fluid to flow into the interior of the barrel of the syringe while preventing fluid from flowing in the opposite direction, while the other valve may enable fluid to flow out of the interior of the barrel while preventing fluid from flowing in the opposite direction. Alternatively, a syringe may include a single valve, which is carried at or near a distal end of its plunger. Methods for using such syringes, including, but not limited to, manual pulsed aspiration methods and manual pulsed delivery methods are also disclosed.

18 Claims, 5 Drawing Sheets

(56) References Cited

U.S. PATENT DOCUMENTS

| | | |
|---|---|---|
| 3,664,774 A | 5/1972 | Tupper et al. |
| 3,782,385 A | 1/1974 | Loyd |
| 3,957,052 A | 5/1976 | Topham |
| 4,373,535 A | 2/1983 | Martell |
| 5,395,379 A | 3/1995 | Deutchman et al. |
| 5,623,969 A | 4/1997 | Raines |
| 5,655,541 A | 8/1997 | Vattuone |
| 5,782,621 A | 7/1998 | Harris |
| 6,099,502 A | 8/2000 | Duchon et al. |
| 6,716,187 B1 * | 4/2004 | Jorgensen et al. ........... 604/6.05 |
| 7,041,084 B2 | 5/2006 | Fojtik |
| 7,278,985 B2 | 10/2007 | Ågerup |
| 7,534,234 B2 | 5/2009 | Fojtik |
| 7,674,247 B2 | 3/2010 | Fojtik |
| 2002/0072719 A1 * | 6/2002 | Douglas et al. ................ 604/257 |
| 2003/0069543 A1 | 4/2003 | Carpenter et al. |
| 2004/0019310 A1 | 1/2004 | Hogendijk |
| 2004/0105769 A1 | 6/2004 | Wu et al. |
| 2004/0267201 A1 | 12/2004 | Agerup |
| 2006/0270996 A1 | 11/2006 | Fojtik |

FOREIGN PATENT DOCUMENTS

| | | |
|---|---|---|
| JP | S14-1473 | 2/1939 |
| JP | S26-6296 | 6/1951 |
| JP | S26-5447 | 9/1951 |
| JP | S62-84435 | 5/1987 |
| JP | H07-100212 A | 4/1995 |
| JP | H10-192395 | 7/1998 |
| JP | H11-503941 A | 4/1999 |
| JP | 2001-314479 A | 11/2001 |
| JP | 2001-520919 | 11/2001 |
| JP | 2003-515421 A | 5/2003 |
| JP | 2005-534379 A | 11/2005 |
| JP | 2008-517653 A | 5/2008 |
| WO | 96/32975 A1 | 10/1996 |
| WO | 2006/047181 A1 | 5/2006 |

OTHER PUBLICATIONS

European Patent Office, "Extended European Search Report," in related European Patent Application No. 11754160.7, Aug. 1, 2013.

* cited by examiner

SYRINGE WITH FLOW CONTROL VALVES AND ASSOCIATED METHODS

TECHNICAL FIELD

The present invention relates generally to manually operated syringes and, more specifically, to manually operated syringes with valves for controlling the flow of fluids into, out of, or through the barrels of such syringes. Syringes that incorporate teachings of the present invention are useful in a variety of methods, including, without limitation, manual pulsed aspiration methods and manual pulsed delivery methods.

SUMMARY

In one aspect, the present invention includes syringes with valves that are oriented and arranged to maximize or optimize force and/or control. In various embodiments, such a syringe includes at least a pair of (i.e., at least two) valves. A first valve may be located at or directly adjacent to a distal opening of a barrel of the syringe, while a second valve may be located on another portion of the barrel, or on or directly adjacent to a distal end of the plunger of the syringe.

More specific embodiments of such a syringe are configured to aspirate and, thus, may be referred to herein as "aspiration syringes." Embodiments of aspiration syringes that incorporate teachings of the present invention may include a first valve, which may also be referred to herein as an "inlet valve," which may be associated with a distal opening of a barrel of the syringe to provide control over the flow of matter (e.g., liquid, other fluid, etc.) into the barrel as a plunger of the syringe is drawn proximally out of an interior of the barrel of the syringe. A second valve of such embodiments, which may also be referred to herein as an "outlet valve," may control the flow of matter (e.g., liquid, air, etc.) out of the barrel as the plunger is forced distally into the barrel.

In some embodiments of aspiration syringes, the inlet valve and outlet valve may comprise one-way valves. For example, the inlet valve may comprise a one-way valve that allows fluid to flow proximally into the distal opening of the barrel of the syringe, while preventing fluid from flowing distally out of the distal opening. A one-way outlet valve may allow fluid to flow out of the interior of the barrel, while preventing fluid from being drawn into the interior of the barrel.

In other embodiments of aspiration syringes, the inlet valve may comprise a flow switch (e.g., a stopcock valve, etc.), which selectively (e.g., under manual control by a user, etc.) controls the flow of fluid into or out of the distal opening of the barrel of the syringe. In an open orientation, a flow switch allows fluid to flow into and/or out of the distal opening of the barrel. When closed, a flow switch prevents fluid from flowing into or out of the distal opening. In a specific embodiment, a syringe of the present invention may include at least one inlet valve that comprises a flow switch and at least one outlet valve that comprises a one-way valve oriented to allow fluid to flow out of the interior of the barrel while preventing fluid from flowing into the interior of the barrel.

In still other embodiments of aspiration syringes, an inlet valve may include a flow switch and a one-way valve in series with one another. When the flow switch of such an embodiment is open, fluid may be drawn into the distal opening of the barrel of the syringe, but not forced out of the interior of the barrel through the distal opening. With the flow switch of such an embodiment is closed, fluid may not be drawn proximally through the distal opening of the barrel or forced distally out of the distal opening of the barrel.

Infusion or injection syringes with two or more valves are also within the scope of the present invention. The valves of infusion or injection syringes that incorporate teachings of the present invention may be located at the same positions as the valves of various embodiments of aspiration syringes of the present invention, but with the positions of the inlet valves and outlet valves reversed; i.e., an outlet valve may be positioned at or adjacent to a distal opening of the barrel of an injection or infusion syringe, while an inlet valve may be positioned at or adjacent to another location of the barrel of an infusion or injection syringe, or at or near a distal end of a plunger of an infusion or injection syringe.

According to another aspect, the present invention includes various embodiments of components of an aspiration syringe with at least two valves, including, but not limited to, embodiments of both barrels and plungers. A barrel may have an inlet valve associated with a distal opening of the barrel. An outlet valve may also communicate with an interior of the barrel. In some embodiments, the outlet valve may be associated with (e.g., secured in place relative to) the barrel. In other embodiments, the outlet valve may be associated with a plunger of the syringe. Embodiments of plungers with valves, including, without limitation, valves that are configured or oriented to enable fluid to flow out of the interior of the barrel of a syringe but not into the interior of the barrel, are also within the scope of the present invention.

The valves of a syringe may be positioned as closely as possible to one another. In embodiments where the valves are both secured with the barrel, they may be located at a distal end of the barrel. In embodiments where one of the valves is located at or as near as possible to the distal end of the plunger, when the plunger is fully inserted (distally) into the barrel, the valve on the plunger will be located close to the valve at or near the distal end of the barrel. In aspiration syringes, such valve placements may minimize the volume within which air may be trapped as a vacuum is formed in the syringe. In injection or infusion syringes, such valve placements may reduce the dead space in which air may be trapped as the barrel of the syringe is filled with fluid (during aspiration) that will subsequently be injected or infused.

The present invention also includes embodiments of syringes in which a single valve is positioned at or directly adjacent to the distal end of the plunger of the syringe, while the barrel of the syringe lacks valves. Air may be purged from the interior of the barrel of such an embodiment of syringe by causing the air to rise to a proximal location within the barrel of the syringe (e.g., by pointing a distal end of the barrel generally downward, etc.), then pushing the plunger distally into the barrel, which forces the air out of the interior of the barrel through the valve.

Systems that include aspiration syringes of the present invention are a further aspect of the present invention. In addition to a syringe, such a system may include a distal communication element, such as a catheter, a needle, or the like, in communication with one or each of the inlet valve and the outlet valve.

In another aspect, the present invention includes various methods for using syringes and systems of the present invention. In an aspiration embodiment of such a method, the plunger of the syringe is forced distally into the interior of the syringe barrel to force air or other fluid substantially from the barrel of the syringe. The air or other fluid flows out of the barrel through the outlet valve, while the inlet valve prevents the air or other fluid from flowing out of the distal opening of the barrel and into any communication element associated with the distal opening of the barrel. In this manner, the plunger of the aspiration syringe may be "set" or "reset," enabling aspiration (via proximal movement of the plunger out of the interior of the barrel) without causing fluid to move distally through a communication element associated with the distal opening of the barrel. In a related embodiment, a syringe with two or more valves or a system including such a syringe may be used to pump fluid. When the plunger of such a syringe is repeatedly moved (e.g., manually, etc.) distally, then proximally through the interior of the barrel, the syringe or system may be used to pump fluid from a source, such as the body of a subject.

Another embodiment of an aspiration method that incorporates teachings of the present invention includes the maximization of a vacuum within the interior of the barrel of a syringe. In such a method, fluid flow into or out of the distal opening of the barrel may be prevented, while fluid (e.g., a gas or gas mixture, such as air, etc.) may be forced out of the interior of the barrel at another location, but not allowed into the interior of the barrel at that location. With each repeated movement of the plunger into (distally through) and out of (proximally through) the interior the barrel, more fluid is removed from the interior of the barrel, further increasing a vacuum generated within the interior of the barrel the next time the plunger is drawn proximally through the barrel. When the valves are positioned close to one another, there may be less space within which air or other gases may be compressed, forcing more of the air or other gases from the interior of the barrel. Such a method may, in some embodiments, be effected with embodiments of syringes in which the inlet valve includes a flow switch.

An injection and/or infusion, or delivery, embodiment of a method of the present invention may include drawing the plunger of a syringe proximally out of the interior of the barrel of the syringe to draw fluid from an exterior source and into the interior of the barrel of the syringe. The fluid may be drawn through an inlet valve associated with the plunger of the syringe or with the barrel of the syringe, at a location adjacent to a distal end of the barrel, but not at or in direct communication with the distal opening of the barrel. As fluid is drawn into the interior of the barrel, an outlet valve located at or in direct communication with the distal opening of the barrel may prevent fluid from an exterior location that communicates with the distal opening (e.g., through a fluid communication element, such as needle, catheter, or the like) from being drawn into the interior of the barrel, thereby optimizing the volume of new fluid that may be drawn into the interior of the barrel. Once the interior of the barrel has been substantially filled with fluid, the plunger may be forced distally into the barrel of the syringe, with the inlet valve preventing the fluid from flowing back into its source. The outlet valve, which is located at or in direct communication with the distal opening of the barrel, enables the fluid to be ejected from the interior of the barrel and out of its distal opening. By repeating movement of the plunger out of (proximally through) and into (distally through) the barrel of a syringe, the syringe may be used to pump fluid to a desired site (e.g., into the body of a subject, etc.).

Other aspects of the present invention, as well as features and advantages of various aspects of the present invention, will become apparent to those of ordinary skill in the art through consideration of the ensuing description, the accompanying drawings, and the appended claims.

DETAILED DESCRIPTION

Figure 1:
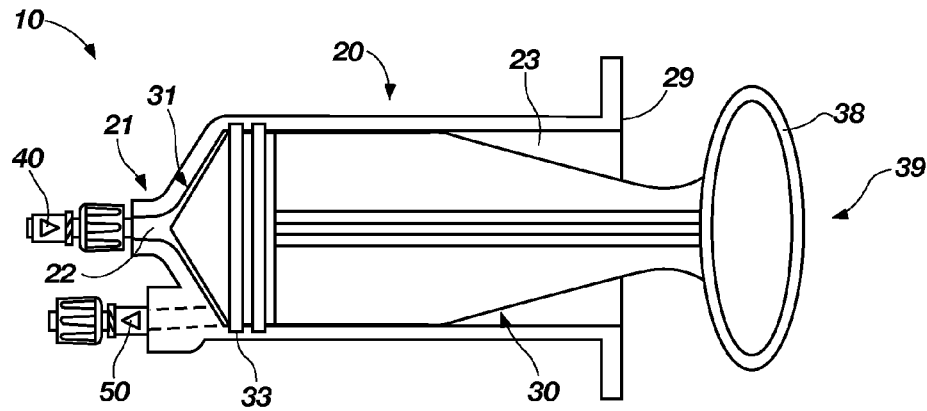
FIG. 1 depicts an embodiment of syringe that includes a barrel with two valves; a plunger of the depicted syringe is fully (distally) inserted into an interior of the barrel of the syringe.
Figure 2:
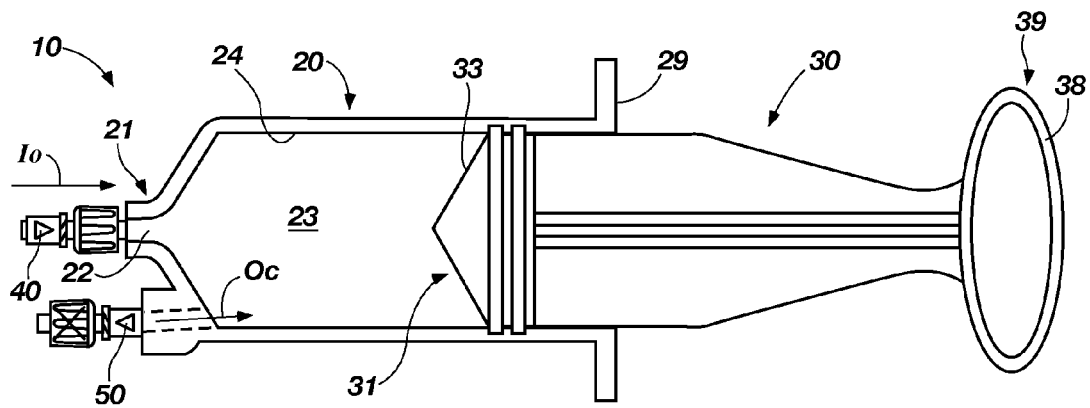
FIG. 2 illustrates the embodiment of syringe shown in FIG. 1, with the plunger being withdrawn (proximally) from the interior the barrel.
Figure 3:
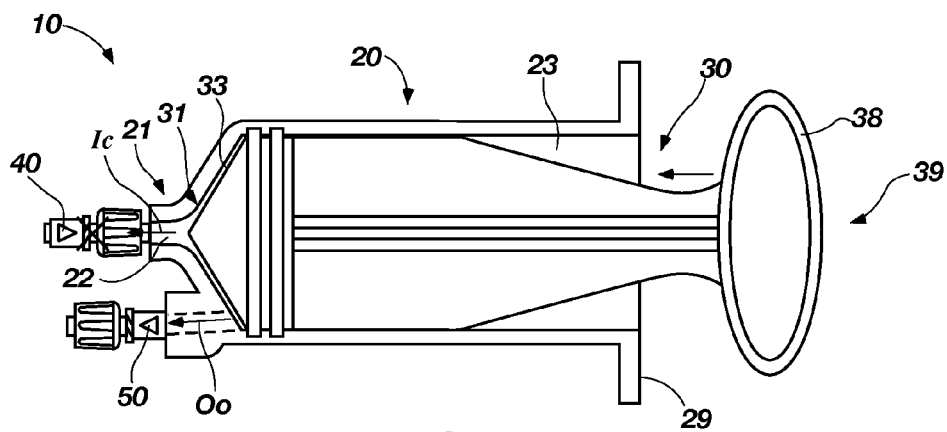
FIG. 3 shows the embodiment of syringe shown in FIGS. 1 and 2, with the plunger being inserted (distally) back into the interior of the barrel.

An embodiment of syringe 10 that incorporates teachings of the present invention is shown in FIGS. 1 through 3 and is described in reference thereto. Syringe 10 includes a barrel 20, a plunger 30, and a pair of valves 40 and 50. Barrel 20 includes a distal end 21 (located away from an individual who operates syringe 10) and a proximal end 29 (located toward an individual who operates syringe 10). At its proximal end 29, barrel 20 includes a proximal opening 28, which communicates with an interior 23 of barrel 20 and is configured to facilitate the introduction of the plunger 30 into the interior 23 of barrel 20. The interior 23 of barrel 20 is configured to receive plunger 30 and to enable plunger 30 to be moved along the length of interior 23 of barrel 20. At its distal end 21, barrel 20 includes a distal opening 22, which is relatively small in size compared to the size of proximal opening 28.

Plunger 30 includes a distal end 31 and a proximal end 39. A tip 33 may be located at the distal end 31 of the plunger 30. Tip 33 may be formed at least partially from a compressible, resilient material (e.g., a rubber, etc.) that substantially seals against an interior surface 24 of barrel 20 to optimize the ability of plunger 30 to draw fluid into the interior 23 of barrel 20 or force fluid from the interior 23 of barrel 20. Tip 33 may also prevent fluid within the interior 23 of barrel 20 from flowing proximally beyond the distal end 31 of plunger 30. At its proximal end 39, plunger 30 includes an actuator 38. In some embodiments, actuator 30 is configured to be grasped by one or more of a user's fingers. In other embodiments, actuator 38 may be configured for assembly with a mechanical actuator, such as a handle (not shown).

In the embodiment of syringe 10 depicted by FIGS. 1 through 3, a first valve 40 is located distally to, and communicates with, distal opening 22 of barrel 20. Valve 40 may comprise a one-way valve that is positioned and oriented to control fluid flow. More specifically, in the embodiment depicted by FIGS. 1 through 3, valve 40 may be positioned and oriented to enable the flow of fluid proximally through the distal opening 22 of barrel 20 and into the interior 23 of barrel 20, while preventing the flow of fluid distally out of the interior 23 and through the distal opening 22 of barrel 20. Thus, in such an embodiment, valve 40 may be termed an "inlet valve." In a specific embodiment, valve 40 may comprise a so-called "duckbill" valve, which, when fluid is applied from an appropriate, "valve opening" direction, opens when the fluid pressure reaches or exceeds a minimum opening threshold pressure, and, when fluid is applied from the opposite, "valve closing" direction, remains closed up to a maximum closed threshold pressure. Of course, the maximum closed threshold pressure is discernibly greater, and may even be significantly greater, than the minimum opening threshold pressure. In a particular embodiment, the minimum opening threshold pressure of valve 40 may be about 20 mm Hg or greater, while the maximum closed threshold pressure of valve 40 may be as great as about 1,000 mm Hg. In another specific embodiment, valve 40 may comprise a switch type valve (e.g., a stopcock valve, etc.), which may be opened or closed. Alternatively, combinations of one-way valves and switch valves may be used.

In addition, a second valve 50 communicates with the interior 23 of barrel 20. As depicted, in at least one embodiment, valve 50 may also be located at distal end 21 of barrel 20. Like valve 40, valve 50 may comprise a one-way valve. Unlike valve 40, valve 50 may be oriented to enable fluid to flow out of the interior 23 of barrel 20, while preventing fluid from flowing into the interior 23 of barrel 20. Thus, in embodiments where valve 50 is so oriented, it may be referred to as an "outlet valve." Valve 50 may, in a specific embodiment, comprise a duckbill valve with a minimum opening threshold pressure of about 20 mm Hg and a maximum closed threshold pressure of about 1000 mm Hg.

Various orientations of plunger 30 relative to the length of barrel 20 are illustrated by FIGS. 1 through 3. FIG. 1 shows syringe 10 with plunger 30 fully inserted into the interior 23 of barrel 20. As plunger 30 is drawn proximally through and, thus, at least partially withdrawn from the interior 23 of barrel 20, as depicted by FIG. 2, sufficient negative pressure may be generated within the interior 23 of barrel 20 to open inlet valve 40 (along arrow $I_O$) and to close valve 50 (along arrow $O_C$), preventing fluid from flowing out of valve 50, as indicated by the symbol X. By moving plunger 30 in this manner, fluid flows proximally, in the direction of arrow $I_O$, through valve 40, through distal opening 22 of barrel 20, and into the interior 23 of barrel 20. Plunger 30 may then be at least partially reinserted into, or moved distally through, the interior 23 of barrel 20 in the manner depicted by FIG. 3, which may generate sufficient positive pressure to cause valve 40 to close (along arrow $I_C$), preventing fluid from flowing out of valve 40, as represented by the symbol X, to open valve 50 (along arrow $O_O$), and to force fluid out of the interior 23 of barrel 20 and through valve 50.

Figure 4:
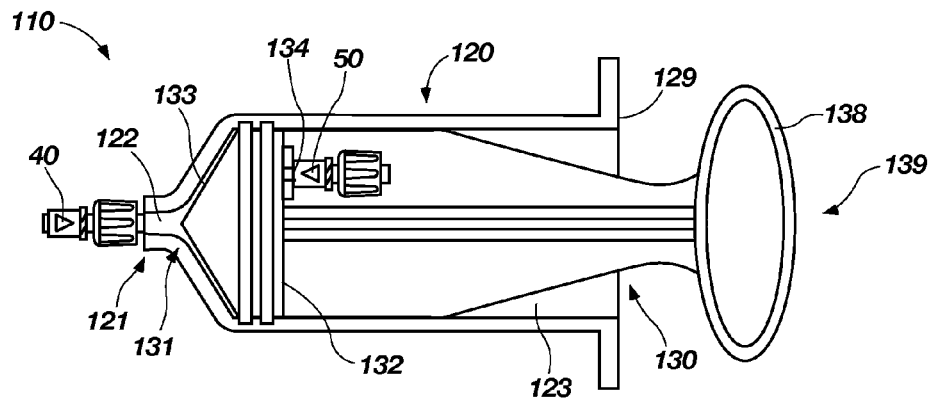
FIG. 4 depicts an embodiment of syringe that includes two valves, one on a barrel of the syringe and the other on the plunger of the syringe; the plunger of the depicted syringe is fully (distally) inserted into an interior of a barrel of the syringe.
Figure 5:
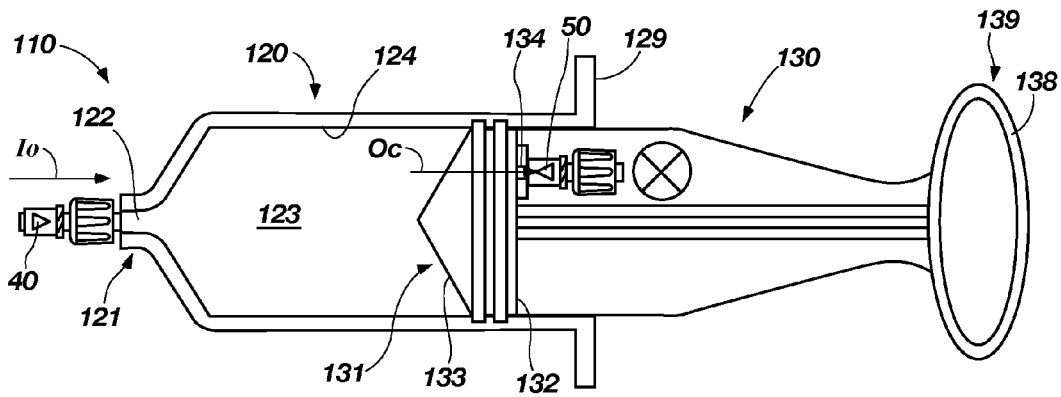
FIG. 5 illustrates the embodiment of syringe shown in FIG. 4, with the plunger being withdrawn (proximally) from the interior of the barrel.
Figure 6:
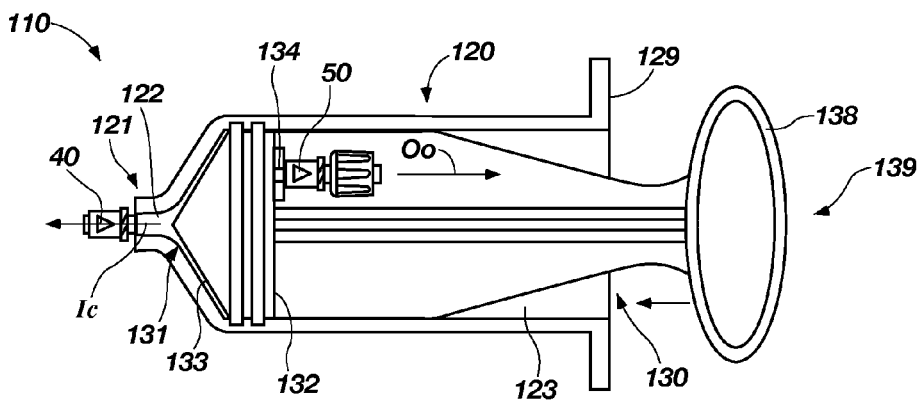
FIG. 6 shows the embodiment of syringe shown in FIGS. 4 and 5, with the plunger being inserted (distally) back into the interior of the barrel.

Turning now to FIGS. 4 through 6, another embodiment of syringe 110 is depicted. Syringe 110 includes a barrel 120 and a plunger 130. Barrel 120 has a distal end 121, at which a distal opening 122 is located, and a proximal end 129, at which a proximal opening 128 is located.

Only one valve 40 is carried by barrel 120. More specifically, an inlet valve may be associated with (e.g., located just distal to, etc.) the distal opening 122 of barrel 120 in a manner that controls the flow of fluid through the distal opening 122. More specifically, valve 40 may be positioned and oriented to enable the flow of fluid proximally through the distal opening 122 of barrel 120 and into the interior 123 of barrel 120, while preventing the flow of fluid distally out of the interior 123 and through the distal opening 122 of barrel 120. Valve 40 may, in some embodiments, comprise a one-way valve, such as a duckbill valve. In a specific embodiment, valve 40 may open when pressure substantially in the direction of arrow $I_O$ reaches or exceeds a minimum opening pressure threshold (e.g., about 20 mm Hg, etc.) and close when pressure is applied to valve 40 substantially in the direction of arrow $I_C$ up to a maximum closed pressure threshold (e.g., about 1,000 mm Hg, etc.). In another specific embodiment, valve 40 may comprise a switch type valve (e.g., a stopcock valve, etc.), which may be opened or closed. In alternative embodiments, valve 40 may include both a one-way valve and a switch type valve.

Another valve 50 is associated with the plunger 130 of syringe 110. In the embodiment depicted by FIGS. 4 through 6, plunger 130 includes a distal end 131 and a proximal end 139. At its proximal end 139, plunger 130 includes an actuator 138. Distal end 131 of plunger 130 may include an enlarged element 132 that carries a tip 133. Tip 133 may comprise a compressible, resilient material (e.g., a rubber, etc.) that substantially seals against an interior surface 124 of barrel 120 to optimize the ability of plunger 130 to draw fluid into the interior 123 of barrel 120 or force fluid from the interior 123 of barrel 120. Tip 132 may also prevent fluid within the interior 123 of barrel 120 from flowing proximally beyond the distal end 131 of plunger 130.

A communication port 134 may extend through the tip 133 and the enlarged element 132 at the distal end 131 of plunger 130. Communication port 134 establishes communication between a distal side of the tip 133 (e.g., a distal portion of the interior 123 of barrel 120) and a proximal side of the tip 133 (e.g., a more proximal portion of the interior 123 of barrel 120). A valve 50 may be associated with communication port 134 so as to control the communication of fluid through the communication port 134. The valve 50 may, in various embodiments, comprise an outlet valve, which enables fluid to flow proximally through the communication port 134 (e.g., proximally out of the interior 123 of barrel 120 (FIG. 4, etc.), while preventing fluid from flowing distally through the communication port 134 (e.g., distally into the interior 123 of barrel 120).

Figure 4A:
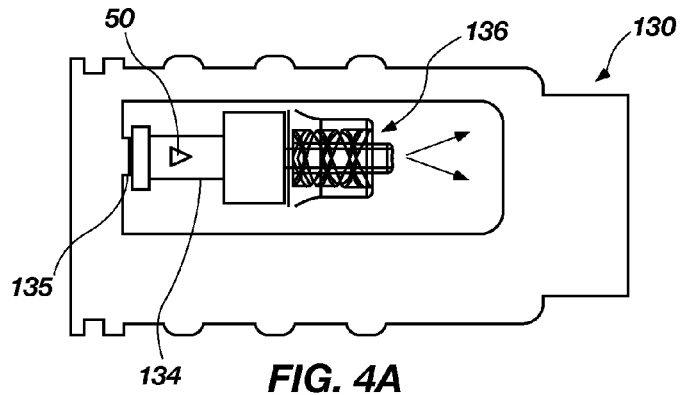
FIG. 4A illustrates specific features of the embodiment of syringe depicted by FIG. 4.

In the specific embodiment depicted by FIG. 4A, communication port 134 extends through a short post 135 that protrudes proximally from the proximal side of the enlarged element 132. A connection member 136 of a coupling element, such as a female member of a luer lock connector, with which valve 50 is associated (e.g., in which valve 50 is seated, otherwise contained, etc.) may be secured to post 135 in any suitable manner. Without limiting the scope of the present invention, the connection member 136 may be screwed onto post 135. Access to the connection member 136 may be obtained as plunger 130 is withdrawn proximally from the interior 123 of barrel 120.

In a specific embodiment, valve 50 may comprise a one-way valve, such as a duckbill valve. Such a valve 50 may open when pressure substantially in the direction of arrow $O_O$ reaches or exceeds a minimum opening pressure threshold (e.g., about 20 mm Hg, etc.) and close when pressure up to a maximum closed pressure threshold (e.g., about 1,000 mm Hg, etc.) is applied to valve 50 in the direction of arrow $O_C$.

FIGS. 4 through 6 show the plunger 130 of syringe 110 at different locations within the interior 123 of the barrel 120 of syringe 110. FIG. 4 shows syringe 110 with plunger 130 fully inserted into the interior 123 of barrel 120. As plunger 130 is drawn proximally through and, thus, at least partially withdrawn from the interior 123 of barrel 120, as depicted by FIG. 5, sufficient negative pressure may be generated within the interior 123 of barrel 120 substantially in the direction of arrow $I_O$ to open valve 40 and substantially in the direction arrow $O_C$ to close valve 50, preventing fluid from flowing out of valve 50, as indicated by the symbol X. Fluid then flows proximally, in the direction of arrow $I_O$, through valve 40, through distal opening 22 of barrel 20, and into the interior 23 of barrel 20. Plunger 30 may then be at least partially reinserted into, or moved distally through, the interior 23 of barrel 20 in the manner depicted by FIG. 6, which may generate sufficient positive pressure to cause valve 40 to close (along arrow $I_C$), preventing fluid from flowing distally out of the interior 123 of barrel 120 through valve 40, as represented by the symbol X; to open valve 50 (along arrow $O_O$); and to force fluid out of the interior 23 of barrel 20 and through valve 50.

By positioning the valves of a syringe that incorporates teachings of the present invention as close as possible to the interior of the barrel, dead space may be reduced or eliminated, and the potential for clogging lengthy conduits may also be reduced or eliminated.

Figure 7:
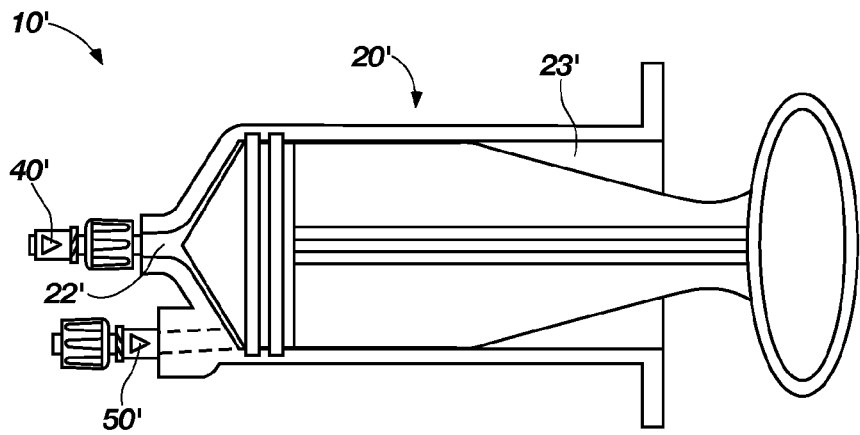
FIGS. 7 and 8 illustrate embodiments of injection/infusion syringes of the present invention.
Figure 8:
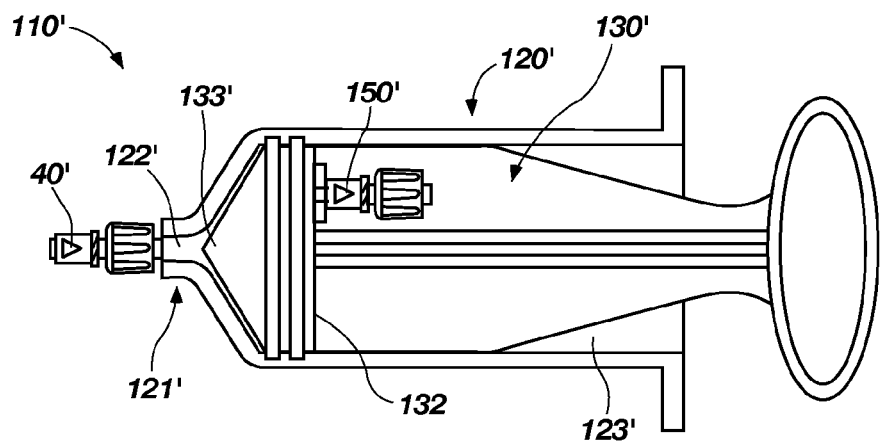

While the disclosure that has been provided above focuses primarily upon syringes with valve systems that are useful for drawing fluid in a proximal direction (i.e., toward the operator of a syringe), valve systems that facilitate the flow of fluid in a distal direction (i.e., away from the operator of a syringe) are also within the scope of the present invention. In the nonlimiting examples shown in FIGS. 7 and 8, various embodiments of syringes 10' and 110', respectively, that incorporate teachings of the present invention may include a first valve 40' oriented to enable fluid to flow distally out of the interior 23', 123' of the barrel 20', 120' of syringe 10', 110', through its distal opening 22', 122'; while preventing the flow of fluid proximally through the distal opening 22', 122' and into the interior 23', 123' of the barrel 20', 120' of syringe 10', 110'. A second valve 50' may be oriented to enable fluid from an external source (not shown) to be drawn into the interior 23', 123' of the barrel 20', 120' of syringe 10', 110' from another location (i.e., a location other than the distal opening of the syringe) while preventing fluid from being removed from the interior 23', 123' of the barrel 20', 120' at that location.

Figure 9:
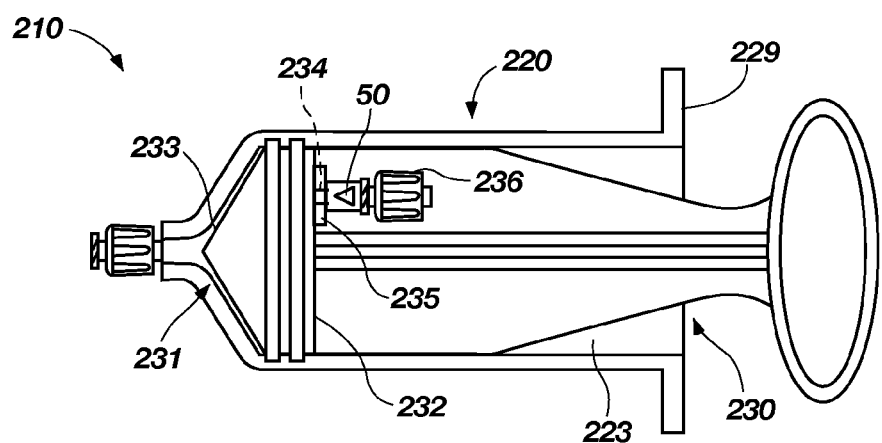
FIG. 9 illustrates an embodiment of syringe that includes a single valve, which is positioned at or adjacent to a distal end of the plunger of that syringe.

Referring now to FIG. 9, an embodiment of syringe 210 that includes a single valve 50 is depicted. In the depicted embodiment, valve 50 is located on the plunger 230 of syringe 210, directly adjacent to a distal end 231 of plunger 230. More specifically, valve 50 may be located on a proximal side of an enlarged element 232 of plunger 230, which carries a tip 233 of plunger 230. Valve 50 may communicate with a portion of an interior 223 of the barrel 220 of syringe 210 located distal to the tip 233 through a communication port 234 that extends through the tip 233 and the enlarged end 232 of plunger 230. In the specific embodiment depicted by FIG. 9, the communication port 234 extends through a short post 235 that protrudes proximally from the proximal side of the enlarged element 232. A connection member 236 of a coupling element, such as a female member of a luer lock connector, with which valve 50 is associated (e.g., in which valve 50 is seated, otherwise contained, etc.) may be secured to post 235 in any suitable manner. Without limiting the scope of the present invention, the connection member 236 may be screwed onto the post 235. Access to the connection member 236 may be obtained as plunger 30 is withdrawn proximally from the interior 223 of barrel 220.

In other embodiments, valve 50 may be oppositely oriented, allowing fluid to flow distally through the communication port 234 and into the interior 223 of barrel 220, while preventing fluid from flowing proximally through the communication port 234, out of the interior 223 of barrel 220. A single valve embodiment may also be configured to improve injection. When the distance between such an inlet valve 50 and the distal end 231 of plunger 230 is minimized, the distance between a source of fluid (e.g., saline, drugs, contrast media, etc.) (not shown) and the interior 223 of barrel 220 is also minimized, which may improve the rate at which fluid flows from the fluid source into the interior 223 of barrel 220.

Valve 50 may comprise an automatic one-way check valve of know type. In some embodiments, valve 50 may be oriented to open as plunger 230 is forced distally into the interior 223 of barrel 220, increasing pressure within the interior 223 of barrel 220. A sufficient increase of pressure within the interior 223 of barrel 220 (e.g., a minimum opening threshold pressure of at least about 20 mm Hg, at least about 40 mm Hg, etc.) causes valve 50 to open, or cracks valve 50, and enables the flow of fluid proximally through the communication port 234 that extends through the tip 233 and enlarged end 232 of plunger 230.

Figure 10:
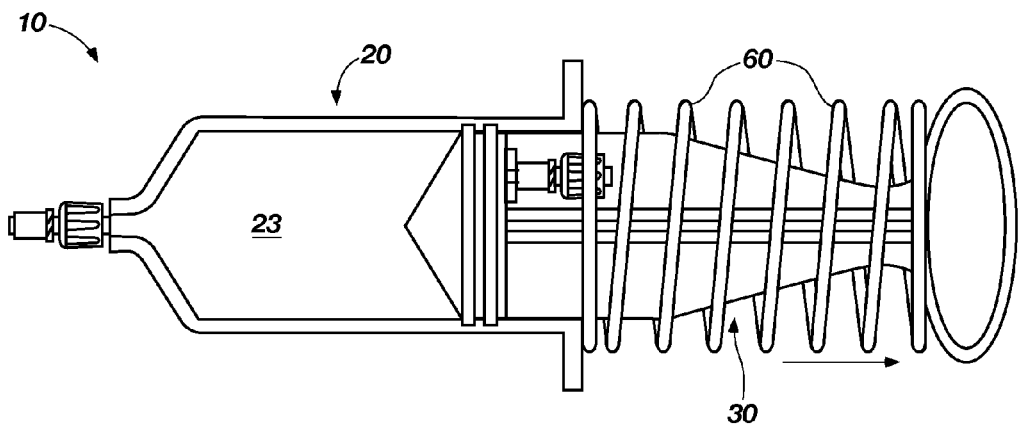
FIG. 10 shows an embodiment of syringe that includes a spring that urges proximal movement of a plunger of the syringe proximally through (out of) a barrel of the syringe.

As shown in FIG. 10, a spring 60 may be associated with any embodiment of syringe that incorporates teachings of the present invention (shown as syringe 10 merely for the sake of simplicity), to urge or facilitate movement of the plunger 30 through the interior 23 of barrel 20 in a direction opposite from the direction that plunger 30 travels during more intuitive operation of syringe 10. In the depicted embodiment, a user would most intuitively operate syringe 10 by forcing plunger 30 distally into the interior 23 of barrel 20, so spring 60 would urge or facilitate movement of plunger 30 in the opposite direction, or proximally through (out of) the interior of barrel 20. Of course, in syringe embodiments where the more intuitive operation causes a plunger to move proximally through (out of) a barrel (as in aspiration syringes), a spring may be associated with the plunger so as to urge or facilitate movement of the plunger distally through (into) the barrel.

Although FIGS. 1 through 10 depict syringes with plungers that are configured to be operated by a user's thumb, various other types of syringes may also embody teachings of the present invention. Without limiting the scope of the present invention, teachings of the present invention may be employed in connection with manually operable syringes that provide a mechanical advantage, such as those described in U.S. Pat. Nos. 7,534,234 and 7,041,084 and in U.S. Patent Application Publication 20060270996, the disclosure of each of which is hereby incorporated herein, in its entirety, by this reference. It should also be noted that teachings of the present invention may apply to aspiration syringes, infusion or injection syringes, and one or both barrels of a multiple barrel syringe, such as the double barrel syringe described in U.S. Pat. No. 7,674,247, the disclosure of which is hereby incorporated herein, in its entirety, by this reference.

Figure 11:
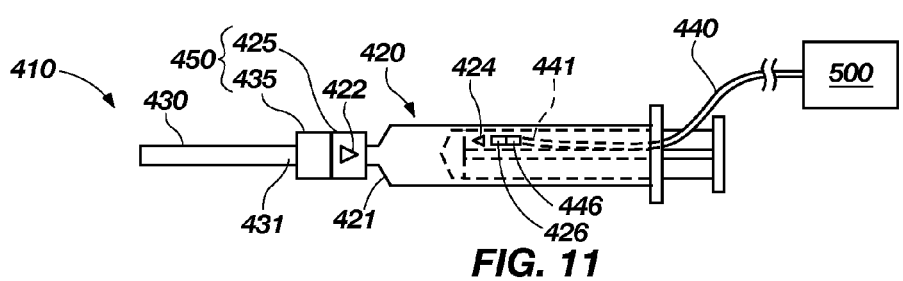
FIGS. 11 and 12 depict embodiments of systems according to the present invention, which include syringes, as well as distal communication elements and, optionally, proximal communication elements.
Figure 12:
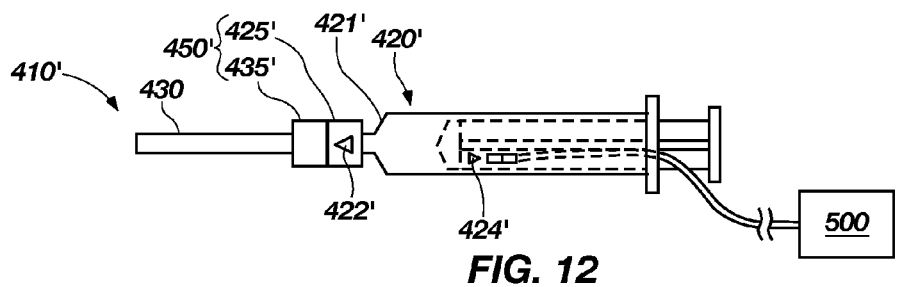

Referring now to FIGS. 11 and 12, embodiments of systems 410, 410' of the present invention are illustrated. Such a system 410, 410' includes a syringe 420, 420' and a distal communication element 430. In some embodiments, such a system 410, 410' may also include a proximal communication element 440.

Syringe 420, 420' includes at least two valves 422 and 424, 422' and 424'. Valves 422 and 424, 422' and 424' may be oriented to enable aspiration or to enable injection and/or infusion. Although two specific embodiments of syringes 420, 420' are illustrated by FIGS. 11 and 12, a system 410, 410' according to embodiments of the present invention may include any other embodiment of syringe that incorporates teachings of the present invention.

Distal communication element 430 may be configured to communicate fluid to or from a desired location. In some embodiments, distal communication element 430 may be configured to communicate fluid from or into the body of a subject. Specific embodiments of such a distal communication element 430 include, but are not limited to, various types of catheters, various types of tubes, various types of needles, trocars, and other apparatus for obtaining samples from a subject or for injecting or infusing fluid into the body of a subject.

A distal communication element 430 may be coupled to communicate directly with a distal opening (see, e.g., FIGS. 1 through 11) in the distal end of the barrel of a syringe 420, 420' and, thus, communicate with an interior of the barrel in any suitable manner known in the art. In some embodiments, a proximal end 431 of distal communication element 430 and a distal end 421, 421' of the barrel of syringe 420, 420' may include mating, or cooperating, parts 435, 435' and 425, 425', respectively, of a coupling element 450, 450', such as a luer lock coupling.

In embodiments where a system 410, 410' of the present invention includes a proximal communication element 440, the proximal communication element 440 may communicate with the interior of the barrel of syringe 420, 420' across valve 424, 424'. In various embodiments, proximal communication element 440 may comprise a tube or other conduit that transfers fluid between the interior of syringe 420, 420' and an external reservoir 500 (e.g., into the interior of the barrel of syringe 420, 420' in an injection or infusion system, out of the interior of the barrel of syringe 420, 420' in an aspiration system, etc.).

Such a proximal communication element 440 may be coupled to syringe 420, 420' in any suitable manner known in the art. Like the distal communication element 430, a distal end 441 of the proximal communication element 440 may include a coupling element 446 that is configured to be coupled to a complementary coupling element 426 on the syringe 420, 420' (e.g., members of a leur lock coupling element, etc.).

With returned reference to FIGS. 1 through 3 (although the method is not limited to use of a particular embodiment of syringe), an embodiment of an aspiration method of the present invention will described. Such a method includes moving plunger 30 of a syringe 10 distally through interior 23 of a barrel 20 of syringe 10 to decrease a volume within interior 23 of barrel 30 between a distal end 21 of barrel 20 and a tip 33 of plunger 30. Movement of plunger 30 in this manner generates a positive pressure within interior 23 of barrel 20, which causes a valve 40 at distal opening 22 of barrel 20 to close and forces air or other fluids out of the interior 23 of barrel 20 through an outlet valve 50 that communicates with the interior 23 of barrel 20.

By moving plunger 30 of a syringe 10 from a distal position within the interior 23 of a barrel 20 of the syringe 10 to a more proximal location, a volume within interior 23 of barrel 20 distal of tip 33 of plunger 30 may then be increased. As the volume between tip 33 of plunger 30 and distal end 21 of barrel 20 increases, a vacuum is created within interior 23 of barrel 20, which may draw fluid through valve 40.

Figure 13:
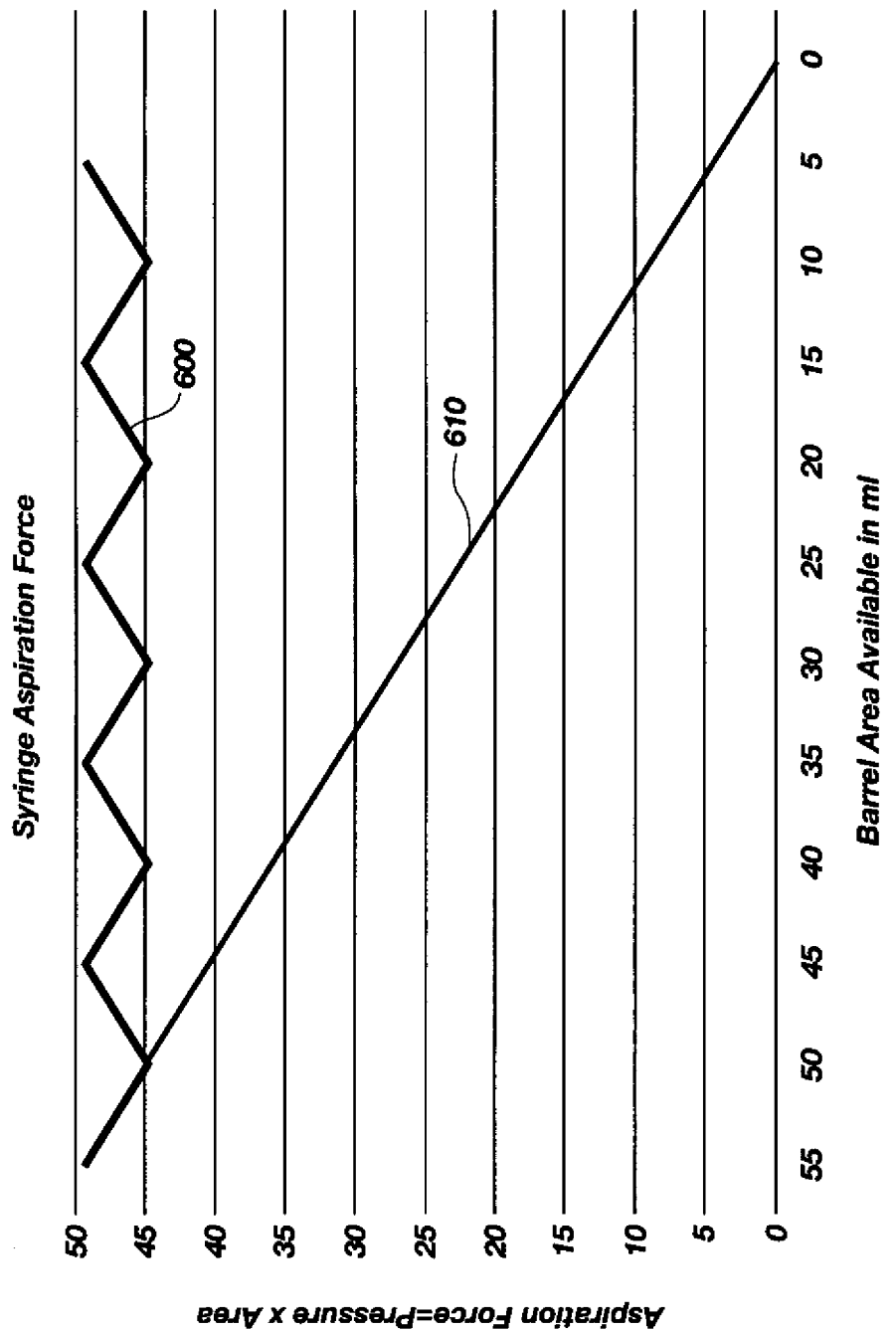
FIG. 13 is a graph illustrating the force that may be generated when manual pulsed aspiration methods are effected in accordance with teachings of the present invention.

In embodiments where valve 40 comprises a one-way valve, repeated movement of the plunger 30 distally into and proximally out of interior 23 of barrel 20 may enable syringe 10 to operate as a manual pump, which may aspirate fluid in a substantially continuous, or pulsed, manner, such as that represented by line 600 in the graph of FIG. 13. Line 610 of that graph, in comparison, shows that the aspiration force of a conventional syringe, in which only a single aspiration stroke of plunger 30 may be made, quickly diminishes to zero, limiting the volume of fluid that may be aspirated with such a syringe. Manually pulsed aspiration with a syringe that incorporates teachings of the present invention provides a user with immediate responsiveness and control over the force with which fluids are aspirated by such a syringe.

Pulsed aspiration is also possible with a single-valve embodiment of a syringe, such as the syringe 210 shown in and described with reference to FIG. 9, particularly where the pressure communicated to the distal end 222 of barrel 220 of such a syringe 210 (e.g., by fluid communicated to distal end 222 by an external communication element (not shown), etc.) exceeds the minimum opening threshold pressure of valve 50.

Syringes that incorporate teachings of the present invention also increase the rates at which fluids flow through external communication elements, such as the distal communication element 430 depicted in FIGS. 11 and 12. By using a syringe that incorporates teachings of the present invention, the amount of pressure (positive or negative) that may be generated by a manually operated syringe may be maximized. That increase in pressure, in turn, increases the rate at which fluid flows through a distal communication element 430, as evidenced by Poiseuille's equation:

$$\Delta P = \frac{8\mu LQ}{\pi r^4} \text{ or } \Delta P = \frac{128\mu LQ}{\pi d^4}$$

where:
    ΔP represents the change, or drop, in pressure from one point along the length of the conduit to a second point along the length of the conduit;
    L is the length of the conduit;
    μ is the dynamic viscosity of the fluid flowing through the conduit;
    Q is the volumetric flow rate at which fluid flows through the conduit;
    r is the radius of the conduit;
    d is the diameter of the conduit; and
    π is the mathematical constant pi, which is about 3.1416, and by Poiseuille's Law, which is represented by the following equation:

$$Q = (\pi \Delta P r^4)/(8\eta L),$$

where:
    L is the length of the conduit; and
    η is viscosity of the fluid.

Manually pulsed aspiration processes may be useful in a variety of procedures. Examples of such procedures include, but are not limited to, general drainage procedures, general suction procedures, and general extraction procedures. More specific examples of such procedures include, without limitation, plural effusions, biliary drainage, aspiration of cysts, abscess removal, thrombus removal, ebolectomy, artherectomy, nephrostomy, lavage, wound evacuation, biopsy (e.g., bone biopsy, etc.), marrow extraction, spinal tap, spinal disc decompression, tissue resection techniques, and liposuction. Manually pulsed aspiration processes may also be used for other purposes, such as to clear and/or clean feeding tubes, access lines, or ports.

The vacuum generated within interior 23 of barrel 20 may be maximized when valve 40 includes a switch type valve that has been oriented in a closed position. When the plunger 30 is initially fully inserted into the interior 23 of the barrel 20, some dead space may be present within the interior 23 of the barrel 20. Since fluid, including air, is typically compressible, a relatively large amount of air may remain within the interior 23 of the barrel 20 even when the volume of the dead space is relatively small. Any air or other fluids that have been compressed within dead space in the interior 23 of the barrel 20 may be allowed to be decompressed and purged from the interior 23 of the barrel 20 by repeated movement of the plunger 30 distally into the interior 23 of the barrel 20 then proximally out of the interior 23 of the barrel 20. Once the desired vacuum has been generated within the interior 23 of the barrel 20, the valve 40 may be opened to enable fluid to be aspirated into the interior 23 of the barrel 20.

Turning again to FIG. 8 (although the method is not limited to use of a particular embodiment of syringe), an injection and/or infusion, or delivery, embodiment of a method of the present invention is described. Such a method may include drawing the plunger 130' of a syringe 110' proximally out of interior 123' of barrel 120' of syringe 110' to draw fluid from an exterior source (not shown) and into interior 123' of barrel 120' of syringe 110'. The fluid may be drawn through an inlet valve 150' that communicates with a portion of interior 123' of barrel 120' located between tip 133'0 of plunger 130'0 and distal end 121'0 of barrel 120'. As fluid is drawn into interior 123'0 of barrel 120', an outlet valve 40' located at or in direct communication with distal opening 122'0 of barrel 120' may prevent fluid from an exterior location that communicates with distal opening 122' (e.g., through a fluid communication element, such as needle, catheter, or the like) from being drawn into interior 123' of barrel 120', thereby optimizing the volume of new fluid that may be drawn into interior 123'0 of barrel 120'. Once interior 123' of barrel 120' has been substantially filled with fluid, plunger 130' may be forced distally into interior 123' of barrel 120' to generate a positive pressure within interior 123' of barrel 120'. The positive pressure created within interior 123' of barrel 120' may cause inlet valve 150' to close, preventing fluid from flowing back into its source. In addition, the positive pressure within interior 123' of barrel 120' causes outlet valve 40' to open and the fluid to flow out of interior 123' of barrel 120' through distal opening 122' of barrel 120'. By repeating movement of plunger 130' out of (proximally through) and into (distally through) interior 123' of barrel 120' of syringe 110', syringe 110' may be used to pump fluid (e.g., manually, etc.) to a desired site (e.g., into the body of a subject, etc.).

Returning reference to FIG. 9, the present invention also includes methods for purging air from the interior 223 of the barrel 220 of a syringe 210. When an embodiment of syringe 210 includes an outlet valve 50 associated with its plunger 230, valve 50 may operate as an outlet that maximizes or optimizes the volume of fluid that may be purged or expelled from the interior 223 of barrel 220 (although an embodiment of such a method is described in reference to FIG. 9, other embodiments of syringes that include valves located on or directly adjacent to the distal end of a plunger, such as those depicted in FIGS. 4 through 6, may also be used in such methods). Such purging or expulsion is possible with a single valve in circumstances when a distal opening 222 of barrel 220 is subjected to a pressure that exceeds the minimum opening threshold pressure of valve 50; for example, when the distal opening 222 of barrel 220 communicates with an external communication element (not shown) (e.g., a needle, trocar, catheter, tube, etc.) that, in turn, communicates to the distal opening 222 a high pressure from a remote location within the body of a subject.

With continued reference to FIG. 9, an embodiment of syringe 210 that includes a single, plunger 230-mounted valve 50 may also enable air to be purged from the interior 223 of barrel 220 regardless of the orientation of syringe 210. Thus, syringe 210 may be oriented in an inverted or partially inverted position (i.e., distal end 221 of barrel 220 down, proximal end 239 of plunger 230 up), which is a more natural orientation for a user than the orientation (i.e., distal end 221 up) that is typically required to purge air from the interior of the barrel of a conventional syringe.

Although the foregoing description contains many specifics, these should not be construed as limiting the scope of the present invention, but merely as providing illustrations of some embodiments. Similarly, other embodiments of the invention may be devised which do not exceed the scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. An aspiration syringe, comprising:
   a barrel for receiving fluid;
   a plunger insertable into the barrel, the plunger configured to be drawn proximally through the barrel to draw fluid into the barrel;
   a first valve associated with a distal end of the barrel, the first valve comprising a one-way valve configured to permit the fluid to flow proximally into the barrel and to prevent the fluid from flowing distally out of or away from the aspiration syringe; and
   a second valve carried by the plunger, the second valve comprising a one-way valve configured to enable fluid to exit a confined interior of the barrel or a system of which the confined interior of the barrel is a part, through the plunger, directly to a proximal portion of the barrel open to an exterior of the aspiration syringe,
   wherein the second valve is configured to couple to a proximal communication element.

2. The aspiration syringe of claim 1, wherein the first valve communicates with a port extending through the barrel, near the distal end of the barrel.

3. The aspiration syringe of claim 1, wherein the first valve is secured to the barrel, near the distal end of the barrel.

4. The aspiration syringe of claim 1, wherein the first valve is associated with a member configured to be removably secured to the distal end of the barrel and is configured to be removably secured at the distal end of the barrel.

5. The aspiration syringe of claim 1, wherein the second valve controls communication of fluid through a distal end of the plunger.

6. The aspiration syringe of claim 5, wherein the second valve communicates with the confined interior of the barrel through a port extending through the distal end of the plunger.

7. The aspiration syringe of claim 6, wherein the second valve is secured to a proximal side of the distal end of the plunger.

8. The aspiration syringe of claim 1, further comprising:
a first connection element associated with the first valve, the first connection element being configured to establish communication between a source exterior to the barrel and an interior of the barrel.

9. The aspiration syringe of claim 1, wherein the first valve comprises a switch type valve.

10. A system for aspirating fluid, comprising:
a distal communication element including:
   a distal end;
   a proximal end; and
a syringe, including:
   a barrel for receiving fluid, the barrel including a distal end configured to communicate with the proximal end of the distal communication element;
   a plunger insertable into a proximal end of the barrel, the plunger configured to be drawn proximally through the barrel to generate a vacuum within the barrel; and
   a pair of valves associated with the barrel,
      a first valve of the pair of valves comprising a one-way valve configured to enable fluid to flow proximally and to prevent fluid from flowing distally; and
      a second valve of the pair of valves comprising a one-way valve configured to enable fluid to flow out of the barrel through the plunger, into a proximal communication element coupled to and in communication with the second valve, and to an exterior of the syringe.

11. The system of claim 10, further comprising:
the proximal communication element coupled to the plunger for receiving fluid from the second valve.

12. The system of claim 10, wherein the syringe further includes:
a spring for urging the plunger proximally through the barrel.

13. A syringe, comprising:
a barrel for receiving fluid;
a plunger insertable into the barrel, the plunger configured to be drawn proximally through the barrel to draw fluid into the barrel;
a first valve associated with a distal end of the barrel, the first valve comprising a one-way valve configured to control the flow of fluid into a distal opening of the barrel; and
a second valve associated with an interior the barrel, the second valve comprising a one-way valve configured to control fluid flow out of the interior of the barrel through the plunger, directly to a proximal portion of the barrel open to an exterior of the syringe, in an opposite direction from a direction in which fluid may flow through the first valve,
wherein a connector immediately adjacent the second valve is configured to attach to a proximal communication element.

14. The syringe of claim 13, wherein:
the first valve is configured to enable fluid to flow into the barrel through the distal opening while preventing fluid from flowing out of the barrel through the distal opening; and
the second valve is configured to enable fluid to flow out of the barrel at a second location while preventing fluid from flowing into the barrel at the second location.

15. The syringe of claim 14, wherein the second valve is carried by the plunger.

16. The syringe of claim 15, wherein the second valve is located at or directly adjacent to a distal end of the plunger.

17. A syringe, comprising:
a barrel for receiving fluid;
a plunger insertable into the barrel, the plunger configured to be drawn proximally through the barrel to draw fluid into the barrel; and
a valve at a distal end of the plunger, the valve communicating with an interior of the barrel and with an exterior of the syringe, the valve comprising a one-way valve configured to enable fluid to exit the barrel while preventing fluid from entering the barrel at the same location,
wherein a connector immediately adjacent the second valve is configured to attach to a proximal communication element.

18. The syringe of claim 17, further comprising:
another valve in direct flow communication with a distal opening of the barrel, the another valve comprising a one-way valve configured to enable fluid to enter the barrel.

* * * * *